US010633416B2

(12) United States Patent
Lin et al.

(10) Patent No.: US 10,633,416 B2
(45) Date of Patent: Apr. 28, 2020

(54) CONOTOXIN POLYPEPTIDE κ-CPTX-BT104, AND METHOD FOR PREPARATION THEREOF AND APPLICATION THEREOF

(71) Applicant: BGI SHENZHEN CO., LIMITED, Guangdong (CN)

(72) Inventors: Zhilong Lin, Guangdong (CN); Bo Wen, Guangdong (CN); Ting Tong, Guangdong (CN); Jie Liu, Guangdong (CN); Chaoqin Du, Guangdong (CN); Fen Mo, Guangdong (CN); Chao Peng, Guangdong (CN); Qiong Shi, Guangdong (CN)

(73) Assignee: BGI Shenzhen Co., Ltd, Guangdong (CN)

(*) Notice: Subject to any disclaimer, the term of this patent is extended or adjusted under 35 U.S.C. 154(b) by 12 days.

(21) Appl. No.: 15/515,667

(22) PCT Filed: Sep. 30, 2014

(86) PCT No.: PCT/CN2014/087991
§ 371 (c)(1),
(2) Date: Mar. 30, 2017

(87) PCT Pub. No.: WO2016/049881
PCT Pub. Date: Apr. 7, 2016

(65) Prior Publication Data
US 2017/0298098 A1    Oct. 19, 2017

(51) Int. Cl.
*A61K 38/08*    (2019.01)
*A61K 38/17*    (2006.01)
*A61K 38/04*    (2006.01)
*C07K 5/00*     (2006.01)
*C07K 7/00*     (2006.01)
*C07K 16/00*    (2006.01)
*C07K 17/00*    (2006.01)
*C07K 1/00*     (2006.01)
*C07K 7/06*     (2006.01)
*C07K 1/18*     (2006.01)
*C07K 1/14*     (2006.01)
*A61K 38/00*    (2006.01)

(52) U.S. Cl.
CPC .............. *C07K 7/06* (2013.01); *A61K 38/08* (2013.01); *C07K 1/14* (2013.01); *C07K 1/18* (2013.01); *A61K 38/00* (2013.01)

(58) Field of Classification Search
None
See application file for complete search history.

(56) References Cited

U.S. PATENT DOCUMENTS 10,179,802 B2 * 1/2019 Liu .................. A61K 38/08
2018/0170963 A1 * 6/2018 Liu .................. A61K 38/08

FOREIGN PATENT DOCUMENTS

| CN | 1796412   | 7/2006 |
| CN | 1796413   | 7/2006 |
| CN | 101205251 | 6/2008 |

OTHER PUBLICATIONS

Anderson et al., J. Bioterr. Biodef. 3:1-4 (2012).*
UniProt Accession No. A0A142C1C8, 2 pages (2016) (Year: 2016).*
Jensen et al., Ther. Adv. Neurol. Disord. 7:97-113 (2014) (Year: 2014).*
Simonneau et al., Brain Res. 412:224-232 (1987) (Year: 1987).*
Recovery.Org.UK, "Types of Addictions: How We Treat Them," available online at https://www.recovery.org.uk/addiction/types-of-addictions/, 3 pages (accessed on Sep. 3, 2018) (Year: 2018).*
Tomlinson, M., "How many types of cancer are there?", available online at http://info.isabelhealthcare.com/blog/how-many-types-of-cancer-are-there-world-cancer-day-2017, 5 pages (2017) (Year: 2017).*
Nature.com "Inflammatory Diseases," available online at https://www.nature.com/subjects/inflammatory-diseases, 6 pages (accessed on Sep. 3, 2018) (Year: 2018).*
MedlinePlus Drug Information, "Nifedipine," available online at https://medlineplus.gov/druginfo/meds/a684028.html, 6 pages (last updated Jul. 2018) (Year: 2018).*
Oleinik, A., ScienceDaily, available online at https://www.sciencedaily.com/releases/2015/01/150114090815.htm, 5 pages (2015) (Year: 2015).*
Pennington, et a., Bioorgan. Medicinal Chem. 26:2738-2758 (2018): (Year: 2018).*
Durek et al., Expert. Opin. Ther. Patents 25:1159-1173 (2015) (Year: 2015).*
PubChem Database, PubChem CID: 16135415, 41 pages (first available 2007) (Year: 2007).*
National Cancer Institute, "Cardiovascular disease," available online at https://www.cancer.gov/publications/dictionaries/cancer-terms/def/cardiovascular-disease, 1 page (accessed on Sep. 3, 2018) (Year: 2018).*
Yamaguchi et al., Epilepsy Res. 11:9-16 (1992) (abstract only) (Year: 1992).*
Crimmins et al., Anal. Chinn. Act 352:21-30 (1997) (Year: 1997).*
Extended European Search Report for EP Application No. 14903256.7 dated Jan. 25, 2018.
Shon et al. "k-Conotoxin PVIIA is a Peptide Inhibiting the Shaker K+ Channel" J. Biol. Chem., vol. 273, No. 1, pp. 33-38, 1998.

* cited by examiner

*Primary Examiner* — James H Alstrum-Acevedo
*Assistant Examiner* — Thea D'Ambrosio
(74) *Attorney, Agent, or Firm* — Kowert, Hood, Munyon, Rankin & Goetzel, P.C.; Mark R. DeLuca

(57) ABSTRACT

Disclosed are a conotoxin polypeptide κ-CPTx-bt104, a method for preparation thereof, and an application thereof. The conotoxin polypeptide of the present invention consists of 11 amino acids, has a molecular weight of 1313.47 daltons, and has the full sequence SLCCPEDRWCC (SEQ ID NO. 1).

9 Claims, 4 Drawing Sheets
Specification includes a Sequence Listing.

CONOTOXIN POLYPEPTIDE κ-CPTX-BT104, AND METHOD FOR PREPARATION THEREOF AND APPLICATION THEREOF

TECHNICAL FIELD

The present invention relates to the field of biochemical and molecular biology, and in particular to a conotoxin polypeptide κ-CPTx-bt104, and method for preparation thereof and application thereof.

BACKGROUND ART

Ion channel is a kind of special hydrophilic protein microchannel on the cell membrane, which is the material basis of the electrical activity of nerve and muscle cells. It is found that the functional and structural abnormalities of ion channel is related to the occurrence and development of many diseases. When its function becomes diminished or enhanced to varying degrees, there will lead to the overall physiological function disorder of the body and the formation of certain congenital or acquired diseases, mainly involving the nerve, muscle, heart, kidney and other systems and organs.

Ion channels may be mainly classified into three categories: voltage-gated, ligand-gated and mechanically gated types. They also may be classified into $Na^+$, $K^+$, $Ca^{2+}$, and $Cl^-$ ion channels according to the type of ions in and out. The sodium channels belong to voltage-gated type, and the function thereof is to maintain excitability of cell membrane and its conduction. The calcium channels may be classified into receptor-regulated type and voltage gated type. The potassium channels are ion channels selectively allowing $K^+$ to go across the membrane, which may be classified into voltage-dependent type and ligand-gated type, and the main function thereof is to regulate the membrane potential and excitability of the cell and systolic and diastolic activity of the smooth muscle. The development of synergistic or antagonistic drugs of a specific ion channel and the study of the intervention therapy with specific ion channel subunit genes have very important guiding significance for exploring the pathophysiology of certain diseases, early diagnosis and discovery of specific treatment drugs.

At present, about 15% of the drugs, including therapeutic drugs for hypertension, arrhythmia, epilepsy, diabetes, urinary incontinence, Parkinson's disease, cancer and the like, are targeted at ion channels. Ion channel drugs are mainly in the following categories: calcium channel drugs (calcium antagonists, channel activators), wherein the calcium antagonists generally belong to cardiovascular drugs, such as verapamil and nifedipine; sodium channel drugs, including local anesthetics (Procaine) and antiarrhythmic drugs (quinidine); potassium channel drugs, having a potential therapeutic effect on angina pectoris, arrhythmia, hypertension, immunosuppression, urinary incontinence and other diseases. In summary, these drugs for current clinical application mainly are chemical drugs having relatively high toxic side effects. In contrast, the polypeptide drugs have high activity, low toxic effect and high specificity, and thus have broad application prospects for development into a variety of ion channel drugs.

Cone snail is also known as "chicken-heart-shaped snail". It is estimated that there are about 500 kinds of cone snails in the world, which mainly grow in the tropical sea area, generally live in the warm sea, and belong to Mollusca, Gastropoda, Prosobranchia, Neogastropoda, Conidae and Conus in taxonomy. There are about 100 kinds of cone snails found in China currently, which are mainly distributed in the sea area near Nansha Islands, Xisha Islands, Hainan Island and Taiwan, and a few distributed in Guangdong and Guangxi coast.

Conopeptide (Conoxin, CTX) is a class of biologically active polypeptide toxins obtained from cone snails, and is mainly used for anesthesia of prey, predation and defense of competitor. Studies have shown that each cone snail may contain 1000 kinds of conotoxin, i.e. there may be more than 500,000 kinds of conotoxins in the world. Conotoxin has the following characteristics: small relative molecular weight, rich in disulfide bonds, stable structure, high activity, high selectivity and ease of synthesis, and can highly efficiently and specifically act on acetylcholine receptors and various receptor subtypes of other neurotransmitters.

Similarly, conotoxin can selectively act on ion channels and other protein receptors, thereby affecting the nerve conduction, and resulting in different physiological effects. For example, ω-Conotoxin can specifically block the voltage-sensitive calcium channel, and thus has great application potential in analgesia, neuroprotection, anti-convulsion and relieving cough as a neurobiological probe. μ-Conotoxin can specifically bind to various subtypes of sodium channels and change their function. The μ-conotoxin PIIIA isomers can block sodium channel NaV1.4, and thus is expected to be used in the field of analgesic treatment for cancer patients. κ-Conotoxin specifically blocks voltage-sensitive potassium ion channels, and plays an important role in cell proliferation. κ-conotoxins-PVIIA can stably control a potassium ion channel protein (HERG) and has the potential to be developed into anti-cancer drug molecules.

The laboratory of professor B. M. Olivera from University of Utah is the birthplace of research on conotoxin and the research began in the 1970's. So far, thousands of conotoxins have been isolated, of which dozens have been applied for US patents. They play an important role in the treatment of chronic pain, epilepsy, stroke, spasm, muscle relaxation, Parkinson's disease, Senile Dementia, depression, addiction, cardiovascular disease, cancer and other diseases. At present, some conotoxin polypeptides have entered into clinical research or have been approved by the FDA as a new drug. Ziconotide, developed by Eisai company, approved by the US FDA in 2004 and marketed in UK in July 2006, is used for treatment of severe chronic pain of patients with no response or poorly tolerance to other drugs. The analgesics MrIA (Xen2174) and CVID (AM336) are in the clinical stage I/II and II respectively, and some of the conotoxins are in the preclinical study stage. The ω-Conotoxin SO3 and α-Conotoxin Lt14a are currently under research as analgesics.

Although current research on conotoxins has achieved some results, development of new conotoxins and exploration of their new functions still have an important role in the exploration of the structure and function of ion channels, in research and development of relevant drugs or their lead compounds acting on ion channels, and also have important significance in study of neurobiology.

SUMMARY

The present invention aims to find a new effect of a new conotoxin on ion channels and to provide a new conotoxin polypeptide κ-CPTx-bt104, which can be used as a potassium channel blocker for treatment of arrhythmia, angina pectoris, hypertension and other diseases.

In order to achieve the above objects, the present invention adopts the following technical schemes:

In one aspect, the present invention provides a conotoxin polypeptide κ-CPTx-bt104, wherein the conotoxin polypeptide is comprised of 11 amino acids, and has a molecular weight of 1313.47 daltons and a complete amino acid sequence of SLCCPEDRWCC (SEQ ID NO. 1).

In another aspect, the present invention provides a preparation method comprising: (1) extraction of conotoxin polypeptides; (2) detection of the conotoxin polypeptides; (3) enrichment of the conotoxin polypeptides; (4) separation, sequencing of the conotoxin polypeptides, and sequence selection of the conotoxin polypeptide of the present invention.

Preferably, the extraction of the conotoxin polypeptides comprises removing venom duct from *Conus betulinus*, placing the same in a polypeptide extracting solution, mixing and separating by centrifugation, and then collecting the supernatant for lyophilization.

Preferably, the polypeptide extracting solution comprises a deionized solution containing 30% of acetonitrile and 0.1% of trifluoroacetic acid, and a protease inhibitor.

Preferably, the detection of the conotoxin polypeptides comprises: re-dissolving the extracted conotoxin polypeptides with an 8M urea solution and detecting the protein content and the molecular weight distribution of the conotoxin polypeptides.

Preferably, the enrichment of the conotoxin polypeptides comprises: subjecting the detected conotoxin polypeptides to a reductive alkylation treatment and then enriching the conotoxin polypeptides by extraction column.

Preferably, the reductive alkylation treatment comprises: adding dithiothreitol at a final concentration of 10 mM, reacting at 56° C. for 1 hour, followed by cooling to room temperature, afterwards, adding iodoacetamide at a final concentration of 55 mM, and then reacting in darkroom at room temperature for 45 min.

Preferably, the separation, sequencing of the conotoxin polypeptides, and sequence selection of the conotoxin polypeptide of the present invention comprises: separating the enriched conotoxin polypeptides by strong cation exchange high performance liquid chromatography, performing mass spectrometry of polypeptides by nano-high performance liquid chromatography-mass spectrometry, and then conducting data analysis and bioinformatics analysis according to the mass spectrometric data generated by mass spectrometry to obtain the complete amino acid sequence of the conotoxin polypeptide.

In addition, the present invention also provides the use of the conotoxin polypeptide in inhibiting electric current of potassium ion channel and in analgesia, as well as the use of the conotoxin polypeptide in the drugs for treatment of pain, epilepsy, stroke, spasm, muscle relaxation, Parkinson's disease, Senile Dementia, depression, addiction, cardiovascular disease, cancer, and inflammatory disease.

The beneficial effects of the present invention include that: the claimed conotoxin polypeptide is derived from a naturally active animal resource, belongs to biologically active peptides, has higher safety and less side-effect than traditional small molecule chemical agents, rarely causes a serious immune response, and has high selectivity and specificity. It can be widely used in ion channel-related diseases due to its beneficial characteristics as follows: simple structure, ease of synthesis and high activity for acting on ion channels. After formation of the combination of two pairs of stable disulfide bonds, it is proved by experiment that it can specifically act on potassium ion channels, and it has application value in inhibiting electric current of potassium ion channels and treatment of pain, epilepsy, stroke, spasm, muscle relaxation, Parkinson's disease, Senile Dementia, depression, addiction, cardiovascular disease, cancer, inflammation and other diseases.

The conotoxin polypeptide κ-CPTx-bt104 of the present invention can be used as a potassium channel blocker for treatment of arrhythmia, angina pectoris, hypertension and other diseases as compared with conotoxin BtX and ViTx, which have been reported as potassium channel opener.

DETAILED DESCRIPTION

Figure 1:
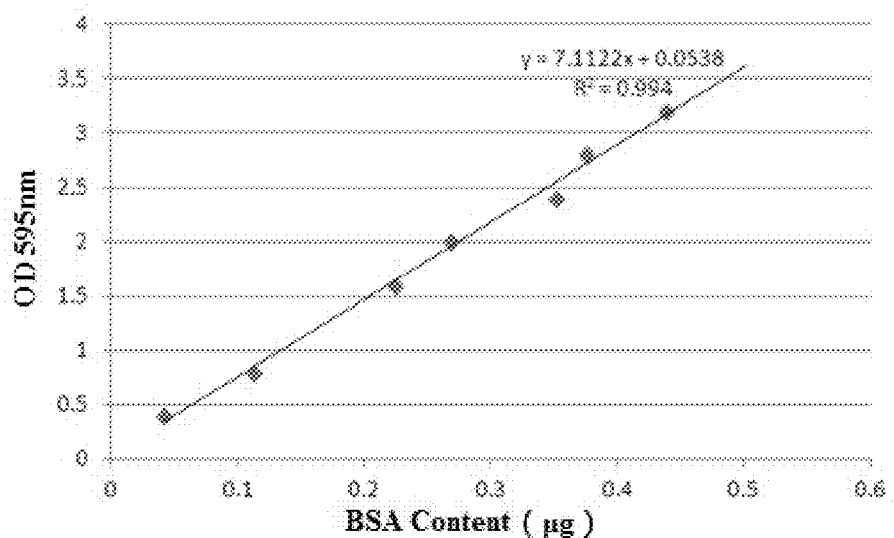
FIG. 1 is a graph showing a Bradford standard curve for determination of protein concentration of the conotoxin polypeptide of the example.

In order to make the objects, technical solutions and advantages of the present invention clearer, the present invention will now be described in further detail with reference to the accompanying drawings and specific examples thereof. It is to be understood that the specific examples described herein are merely illustrative of the invention and are not to be construed as limiting the invention.

A conotoxin polypeptide κ-CPTx-bt104 is comprised of 11 amino acids, has a molecular weight of 1313.47 daltons and a complete amino acid sequence of SLCCPEDRWCC (SEQ. ID NO. 1).

In a specific embodiment, the conotoxin polypeptide κ-CPTx-bt104 is prepared as follows:

*Conus betulinus* growing in Hainan are collected and dissected and their venom ducts are clipped, followed by being cut into pieces and put into polypeptide extracting solution (30% acetonitrile (CAN) and 0.1% trifluoroacetic acid (TFA) in deionized water, containing protease inhibitors), after vortex shock to mix well, centrifuged at 10000 g under 4° C. for 10 min, and then the supernatant is removed and lyophilized.

Afterwards, re-dissolution is performed with an 8M urea solution and the protein content and the molecular weight distribution are detected by Bradford method and SDS-polyacrylamide gel.

After the reductive alkylation treatment is performed with dithiothreitol (DTT, 56° C. water bath for 1 hour, at a final concentration of 10 mM) and iodoacetamide (IAM, reacting in darkroom at room temperature for 45 minutes, at a final concentration of 55 mM), the purified conotoxin polypeptides are obtained by enrichment with Strata-X C18 extraction column.

After the purified conotoxin polypeptides are enriched, components therein are separated by strong cation exchange high performance liquid chromatography (SCX-HPLC), and then subjected to mass spectrometry of polypeptides by nano-high performance liquid chromatography-mass spectrometry (nano LC-MS/MS). The mass spectrometric data generated by mass spectrometry are subjected to data analysis and bioinformatics analysis to obtain the complete amino acid sequence of the conotoxin polypeptide.

The obtained conotoxin polypeptide κ-CPTx-bt104 is subjected to chemical synthesis and renaturation, and then its inhibitory activity on potassium channel is tested.

In particular, the complete sequence of the conotoxin polypeptide is chemically synthesized by standard amino acid resin chemical synthesis method. The synthesized conotoxin polypeptide is redissolved, then detected by ESI-MS (Shimadzu LCMS-2010EV), and then purified through C18 column, and then the purity thereof is detected by RP-HPLC (Shimazu SPD-10AVP). The molecular weight and sequence are then further confirmed by MALDI-TOF MS/MS.

The renaturation process of the conotoxin polypeptide specifically includes: the chemically synthesized conotoxin polypeptide with the primary structure is subjected to renaturation to restore its structure having active effect in natural state. The specific renaturation method is: dissolving the synthesized conotoxin polypeptide at a mass/volume ratio of 1:10 with a renaturation solution (0.1 M Tris-HCl, 0.1 M NaCl, 5 mM GSH, 0.5 mM GSSG, pH 7.4) and then reacting at 25° C. for 24~48 hours. The conotoxin polypeptide after renaturation is detected for the renaturation efficiency by MALDI-TOF-MS. The conotoxin polypeptide after renaturation is further purified by Strata-X C18 extraction column.

In particular, the detection of inhibitory activity of the conotoxin polypeptide on the ion channels includes: using whole-cell patch clamp method to detect the effect of the conotoxin polypeptide on ion channels in dorsal root ganglion cells (DRG cells). The extracellular fluid consisting of 140 mM NaCl, 4 mM KCl, 1 mM $MgCl_2$, 2 mM $CaCl_2$, 5 mM D-Glucose monohydrate, 10 mM 4-hydroxyethyl piperazine ethyl sulfonic acid (HEPES), pH=7.4 is used. The intracellular fluid consists of: 20 mM KCl, 110 mM K-aspartic acid, 1 mM $MgCl_2$, 5 mM ethylene glycol bis(2-aminoethyl ether)tetraacetic acid (EGTA), 10 mM HEPES, pH=7.2.

DRG cells (dorsal root ganglion cells immediately isolated from SD rats and cultured) are removed from a thermostatic incubator and the culture medium in the culture dish is replaced with a well-balanced extracellular fluid at room temperature to prevent drastic changes in temperature of the solution. The extracellular fluid is gently added with a pipette along the wall of the dish to prevent the cells from falling off from the bottom of the dish. The cells after replacement of the medium are observed with an inverted microscope, and the cells with smooth cell membrane and homogeneous cytoplasm are selected for use in a patch clamp test at a room temperature of 20-25° C.

100 μl of borosilicate chunk glass is selected as a glass microelectrode material. A two-step drawing is performed by a drawing instrument to make the diameter of the electrode tip be about 1.5-3.0 μm and the initial resistance of the glass microelectrode after entering a liquid be 2-4 MΩ. After the electrode is filled, installed and moved into the liquid surface, a continuous positive pressure is immediately applied to ensure that the electrode tip is clean, that is, to compensate for the liquid junction potential. Under the inverted microscope, a microelectrode is moved over the selected cell and close to the cell, the positive pressure is removed and a negative pressure is slightly applied for attraction. After a Giga-Ohm (GΩ) seal with high impedance is formed between the electrode and the cell membrane, fast capacitance compensation of the electrode is conducted immediately. The cell is then clamped at −60 mV, a short and strong negative pressure is applied, thereby the cell membrane clamped in the microelectrode is rapidly broken, and then slow capacitance compensation is performed on the cell. After the whole cell recording pattern is formed, the cell is clamped at −90 mV for 4-6 min and then the electric current is recorded. The series resistance (Rs) is always constant within the range of <10 MΩ during the experiment and the system series resistance compensation (Rseries compensation) is between 30% and 70%.

The conotoxin polypeptide of the present invention is derived from a naturally active animal resource, belongs to biologically active peptides, has higher safety and less side-effect than traditional small molecule chemical agents, rarely causes a serious immune response, and has high selectivity and specificity. It can be widely used in ion channel-related diseases due to its beneficial characteristics as follows: simple structure, ease of synthesis and high activity for acting on ion channels. After formation of the combination of two pairs of stable disulfide bonds, it is proved by experiment that it can specifically act on potassium ion channels, and it has application value in inhibiting electric current of potassium channels and treatment of pain, epilepsy, stroke, spasm, muscle relaxation, Parkinson's disease, Senile Dementia, depression, addiction, cardiovascular disease, cancer, inflammation and other diseases

EXAMPLES

The specific preparation steps of the conotoxin polypeptide κ-CPTx-bt104 are as follows:
(1) Extraction of the Conotoxin Polypeptides Four *Conus betulinus* growing in Hainan were dissected after smashing their shells, and their venom ducts were clipped, simply rinsed by $ddH_2O$ and then put into 800 μl of pre-cooled extraction buffer (0.1% TFA, 30% ACN, and mixture of protease inhibitors). The venom ducts were cut into pieces and then venom therein was squeezed out with a tweezer and dissolved in the extraction buffer, vortexed and mixed well, and then centrifuged at 10000 g under 4° C. for 10 min. The supernatant, as the toxin extracts, was collected and subjected to lyophilization.
(2) Detection of the Conotoxin Polypeptides The extracted conotoxin polypeptides were redissolved with 8 M urea (0.1 M Tris-HCl, pH 8.5). The protein content of the conotoxin polypeptides was determined by the Bradford method. Specifically, 0.2 μg/μl bovine serum albumin (BSA) solution was used as the mother liquor for preparing a group of BSA solutions with gradient concentration. The absorbances of the group of the solutions were detected at 595 nm and a standard curve of protein concentration vs. absorbance was plotted. The absorbance of the sample with unknown protein concentration was detected and the protein concentration was obtained according to the standard curve. The total protein concentration was 16.2 μg/μl, as obtained from the standard curve, and the total volume was 400 μl, that is, the total protein amount was 6.48 mg, as shown in FIG. 1.

Figure 2:
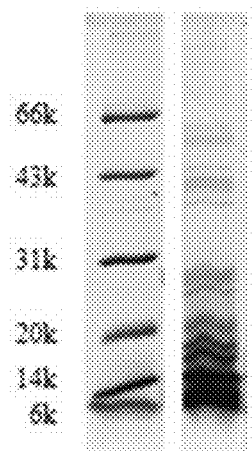
FIG. 2 is a graph showing results of SDS-PAGE detection of the conotoxin polypeptide of the example.

The molecular weight distribution of the conotoxin polypeptides was determined by SDS-polyacrylamide gel. Specifically, a separating gel and a concentrating gel with a width of 7 cm and a thickness of 1 mm were formulated, and the gel concentrations of the two gels were 12% and 5% respectively. An electrophoresis process was conducted by using Bio Rad electrophoresis device, wherein the electrophoresis program was set as follows: 0-20 min, 80V voltage for concentration electrophoresis; and 20-70 min, 120 voltage for separation electrophoresis. The loading amounts of the marker (6-66 KDa) and the sample were 10 ug and 20 ug respectively. After electrophoresis, the gel was stained with Coomassie Brilliant Blue for 2 hours on a shaker and then decolored with a decolorization solution (8% acetic acid+ 25% aqueous ethanol) for 3 times until the gel background became transparent. Electrophoretic results were shown in FIG. 2, from which it can be seen that the electrophoresis bands of the conotoxin proteins were clear, indicating that no degradation occurred, and most of them were peptide components with small molecular weights.

(3) Enrichment of the Conotoxin Polypeptides

The conotoxin polypeptides with a total protein amount of 500 μg were diluted to 200 μl with 8M urea, followed by adding 2 μl of 1M DTT (with a final concentration of 10 mM) thereto, reacting at 56° C. for 1 h, cooling to room temperature and then adding 20 μl of 550 mM IAM (with a final concentration of 55 mM), reacting in darkroom at room temperature for 45 min, without precipitation phenomenon.

The above conotoxin polypeptides were diluted to 1 ml with 8M urea. According to the standard operating procedures for enrichment with Strata-X C18, firstly, the column was activated with 1 ml methanol, then 1 ml of 0.1% FA was added to make it balanced, and then 1 ml of the conotoxin polypeptide sample was loaded thereon, followed by washing with buffer (5% ACN+0.1% FA) for 3 times, and finally the conotoxin polypeptides were eluted with 100% ACN.

The molecular weights and concentrations of the enriched conotoxin polypeptides were examined by MALDI-TOF-MS and Nanodrop (Thermo Scientific). The detection range of molecular weight by MALDI-TOF-MS is 700 to 3500 daltons. 1 μl of the sample was loaded on the plate and dried, then matrix (saturated CHCA) was added, and then the standard was loaded and dried, followed by detection. The specific detection results were shown in FIG. 3.

The above steps were repeated to obtain two samples of T1 and T2. According to the standard operating procedures for polypeptide concentration determination with Nanodrop 8000, the concentration was detected at A280 and the results were shown in Table 1.

TABLE 1

Detection results of conotoxin polypeptides by Nanodrop (A280)

| Sample | Concentration (ug/ul) | Volume (ul) |
|---|---|---|
| T1 | 3.049 | 200 |
| T2 | 2.607 | 200 |

(4) Separation, Sequencing of the Conotoxin Polypeptides and Sequence Selection of the Conotoxin Polypeptide of the Present Invention:

240 μg of the conotoxin polypeptides (two samples of T1 and T2) were fractionated by SCX-HPLC (Shimadzu) system (shown in Table 2). Before loading, the conotoxin polypeptides were diluted with strong cation exchange buffer A (10 mM $KH_2PO_4$ in 25% ACN, pH 3.5). Buffer B further contained 500 mM potassium chloride on the basis of Buffer A. During separation, firstly, buffer B at 0-40% was used to separate at 1 ml/min for 10 min in a linear binary gradient, followed by reacting with Buffer B at a concentration of 40-90% for 2 min, and then with Buffer B at a concentration of 90% for 3 min, and finally, performing absorbance detection at 214 nm and collecting 10 fractions by gradient elution. The collected fractions were dried with a SCANVAC concentrator, redissolved with 0.1% formic acid, and desalted by C18 solid phase extraction column (Strata-X, Phenomenex), and the desalted conotoxin polypeptides were dried and concentrated, and then re-dissolved with 30 μl of 0.1% formic acid. The obtained solution was analyzed by nanoLC-MS/MS.

TABLE 2 loading amounts of the conotoxin polypeptide samples for separation

| Sample | Concentration (ug/ul) | Injection mass (ug) | Injection volume (ul) |
|---|---|---|---|
| T1 | 3.049 | 240 | 80 |
| T2 | 2.607 | 240 | 92 |

The nanoLC-MS/MS analysis specifically includes the analyses with Shimadzu's nano HPLC chromatograph system and with AB Sciex's Triple TOF 5600 mass spectrometer system. Components of each pre-separated conotoxin polypeptide sample were separated by a self-made Ultimate capillary column with a length of 12 cm, an inner diameter of 75 μm, and filled with Welch Materials brand XB-C18 column material with a particle size of 3 μm and a pore size of 120 A at a flow rate of 300 nl/min. The injection volume was 25 μl and the concentration of Buffer B was increased from 5% to 45% for 40 min gradually for a gradient elution. The electrospray voltage was 2.5 kV, the auxiliary air pressure was 30 PSI, the sheath gas pressure was 15 PSI, and the source temperature was 150° C. for mass spectrum acquisition. The first-order mass spectrum was acquired using a high-resolution mode greater than or equal to 30,000. The valence state of parent ions in the range of 2 charges to 5 charges was selected for acquisition of the second-order mass spectrum. before 30 successive second-order mass spectrometric fragmentation, the first-order mass spectrum was scanned once, as such 30 scans of the second-order spectrum daughter ions were completed in 250 ms, and more than 120 pieces of the second-order spectrums can be produced per second, and the total cycle time was 3.3 seconds.

The original mass spectrometry data obtained by nanoLC-MS/MS detection was converted into MGF format and then Mascot search software was used for data search and identification. In the obtained polypeptide sequences, the conotoxin polypeptide κ-CPTx-bt104 having a full length amino acid sequence of SLCCPEDRWCC (SEQ. ID NO. 1) was selected by sequence characteristic analysis.

The obtained conotoxin polypeptide κ-CPTx-bt104 was subjected to chemical synthesis and renaturation, and then its inhibitory activity on potassium ion channel was tested.

The chemical synthesis of the conotoxin polypeptide included: after the conotoxin polypeptide κ-CPTx-bt104 with a full length amino acid sequence of SLCCPEDRWCC (SEQ. ID NO. 1) was obtained, the complete sequence thereof was synthesized by standard amino acid resin chemical synthesis method (customized by GL Biochem (Shanghai) Ltd.). The molecular weight of the synthetic conotoxin polypeptide was determined by using MALDI-TOF MS, as shown in FIG. 4.

The renaturation process of the conotoxin polypeptide included: the chemically synthesized conotoxin polypeptide with the primary structure was subjected to renaturation to restore its structure having active effect in natural state. The specific renaturation method was: dissolving the synthesized conotoxin polypeptide at a mass/volume ratio of 1:10 using a renaturation solution (0.1 M Tris-HCl, 0.1 M NaCl, 5 mM GSH, 0.5 mM GSSG, pH 7.4) and then reacting at 25° C. for 24~48 hours.

Figure 5:
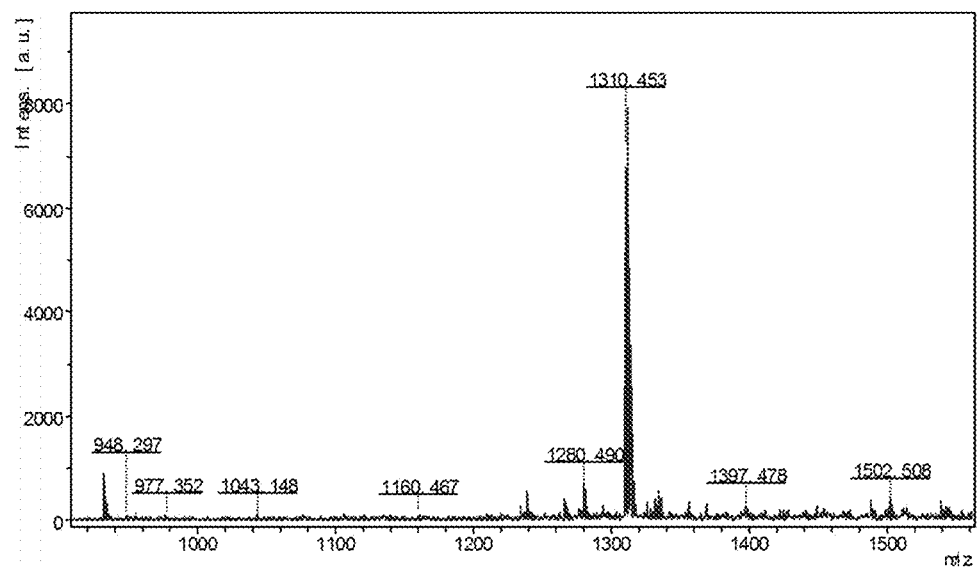
FIG. 5 is a graph showing results of MALDI-TOF-MS detection of the conotoxin polypeptide after renaturation according to the example.

The conotoxin polypeptide after renaturation was detected for the renaturation efficiency by MALDI-TOF-MS. The detection results were shown in FIG. 5. The conotoxin polypeptide after renaturation was further purified by Strata-X C18 extraction column.

Figure 3:
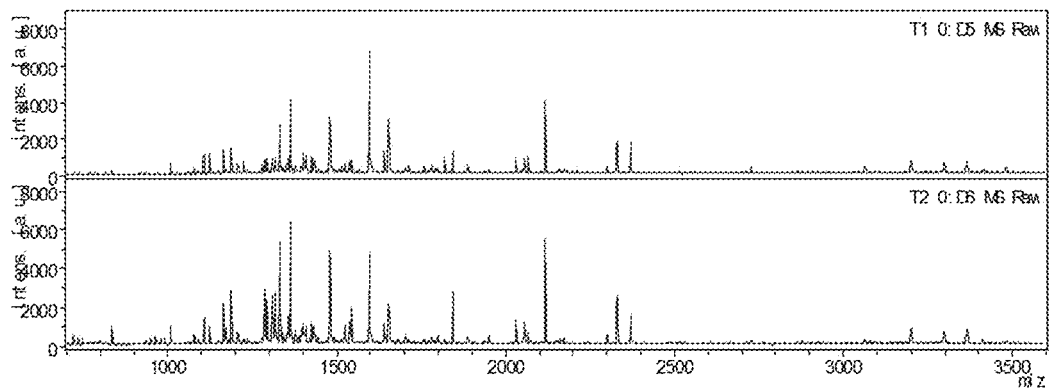
FIG. 3 is a graph showing results of MALDI-TOF-MS detection of the conotoxin polypeptide extracted according to the example.
Figure 4:
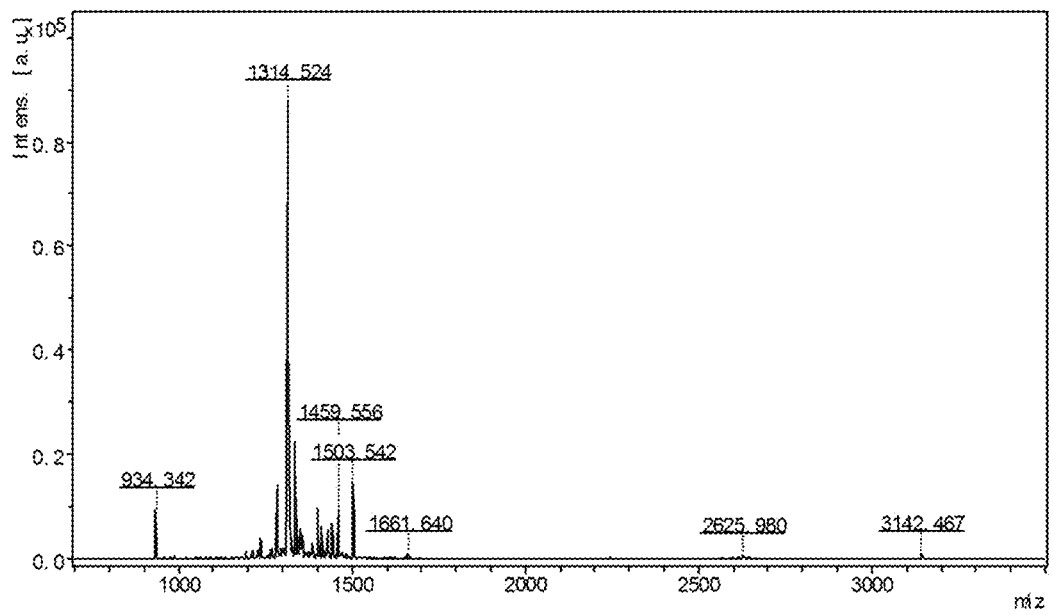
FIG. 4 is a graph showing results of MALDI-TOF-MS detection of the conotoxin polypeptide after chemical synthesis according to the example.
Figure 6:
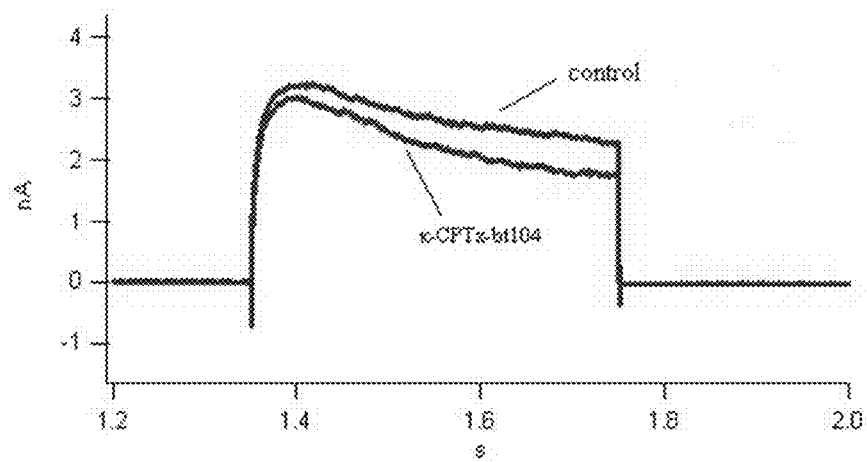
FIG. 6 is a graph showing results of patch clamp detection of inhibitory activity of the conotoxin polypeptide of the example on potassium channel.
Figure 7:
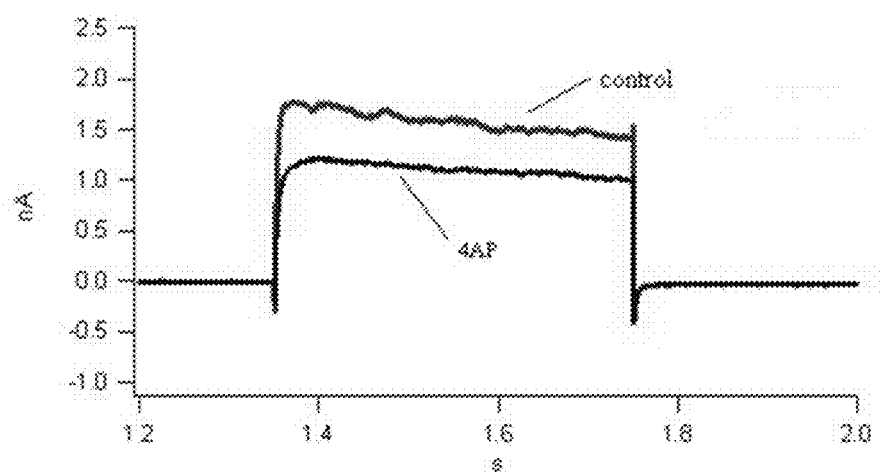
FIG. 7 is a graph showing results of patch clamp detection of inhibitory activity of 4-aminopyridine on potassium channel.

In particular, the detection of inhibitory activity of the polypeptide on the ion channels by patch clamp included: the synthesized conotoxin polypeptide after renaturation was formulated into a solution at a final concentration of 10 μM for detection by a whole-cell patch clamp method. The effect of the conotoxin polypeptide κ-CPTx-bt104 on DRG neuronal ion channels was detected. Meanwhile, 4-aminopyridine (4 AP) was used as the positive control, and the effect of 4-aminopyridine on DRG neuronal ion channels was also detected. The detection results of the conotoxin polypeptide κ-CPTx-bt104 were shown in FIG. 6 and the detection results of the 4AP were shown in FIG. 7, in both of which the control curve represented the potassium ion channel current of the DRG cells recorded before loading as a negative control. FIG. 3 showed the patch clamp detection results of the inhibition rate of κ-CPTx-bt104 on the potassium ion channel current. It can be seen that the inhibitory rate of 10 μM κ-CPTx-bt104 on the potassium ion channel current of the DRG neurons was 0.249.

TABLE 3

Patch clamp detection results of the inhibition rate on potassium ion channel current

| Sample | Concentration | Current recorded before loading (nA) | Current recorded after loading (nA) | Current inhibition rate |
|---|---|---|---|---|
| κ-CPTx-bt105 | 10 μM | 2.45329 | 1.84336 | 0.249 |
| 4AP | 5 mM | 1.47494 | 0.976575 | 0.338 |

The specific embodiments of the invention described above are not to be construed as limiting the scope of the invention. Any other changes and modifications that may be made in accordance with the technical concept of the invention are intended to be included within the scope of the appended claims.

The invention claimed is:

1. A method for preparing a conotoxin polypeptide κ-CPTx-bt104 which consists of 11 amino acids, and has a molecular weight of 1313.47 daltons and a complete amino acid sequence of SLCCPEDRWCC (SEQ. ID NO: 1), characterized in that the method comprises: (1) extraction of conotoxin polypeptides; (2) detection of the conotoxin polypeptides; (3) enrichment of the conotoxin polypeptides; and (4) separation, sequencing of the conotoxin polypeptides and sequence selection of the conotoxin polypeptide.

2. The method for preparing the conotoxin polypeptide according to claim 1, characterized in that the extraction of the conotoxin polypeptides comprises removing the venom duct from *conus betulinus*, placing the same in a polypeptide extracting solution, mixing and separating by centrifugation, and then collecting the supernatant for lyophilization.

3. The method for preparing the conotoxin polypeptide according to claim 2, wherein the polypeptide extracting solution comprises a deionized solution containing 30% of acetonitrile and 0.1% of trifluoroacetic acid, and a protease inhibitor.

4. The method for preparing the conotoxin polypeptide according to claim 1, wherein the detection of the conotoxin polypeptides comprises: re-dissolving the extracted conotoxin polypeptides with an 8M urea solution and detecting the protein content and the molecular weight distribution of the conotoxin polypeptides.

5. The method for preparing the conotoxin polypeptide according to claim 1, wherein the enrichment of the conotoxin polypeptides comprises: subjecting the detected conotoxin polypeptides to a reductive alkylation treatment and then enriching the conotoxin polypeptides by extraction column.

6. The method for preparing the conotoxin polypeptide according to claim 5, wherein the reductive alkylation treatment comprises: adding dithiothreitol at a final concentration of 10 mM, reacting at 56° C. for 1 hour, followed by cooling to room temperature, adding iodoacetamide at a final concentration of 55 mM after cooled to room temperature, and then reacting in a darkroom at room temperature for 45 min.

7. The method for preparing the conotoxin polypeptide according to claim 1, characterized in that the separation, sequencing of the conotoxin polypeptides, and sequence selection of the conotoxin polypeptide comprises: separating the enriched conotoxin polypeptides by strong cation exchange high performance liquid chromatography, performing mass spectrometry of polypeptides by nano-high performance liquid chromatography-mass spectrometry, and then conducting data analysis and bioinformatics analysis

SEQUENCE LISTING

```
<160> NUMBER OF SEQ ID NOS: 1

<210> SEQ ID NO 1
<211> LENGTH: 11
<212> TYPE: PRT
<213> ORGANISM: Conus betulinus

<400> SEQUENCE: 1

Ser Leu Cys Cys Pro Glu Asp Arg Trp Cys Cys
1               5                   10
``` according to the mass spectrometric data generated by mass spectrometry, to obtain the complete amino acid sequence of the conotoxin polypeptide.

8. A method of inhibiting current of a potassium ion channel by administering to a subject a conotoxin polypeptide κ-CPTx-bt104 which consists of 11 amino acids, and has a molecular weight of 1313.47 daltons and a complete amino acid sequence of SLCCPEDRWCC (SEQ. ID NO: 1).

9. A method of treating a condition in a subject in need thereof by administering a conotoxin polypeptide κ-CPTx-bt104 which consists of 11 amino acids, and has a molecular weight of 1313.47 daltons and a complete amino acid sequence of SLCCPEDRWCC (SEQ. ID NO: 1) to the subject, wherein the condition to be treated is selected from the group consisting of muscle relaxation, cardiovascular disease associated with hypertension, and stroke associated with hypertension.

* * * * *